(12) United States Patent
Goto

(10) Patent No.: US 8,838,253 B2
(45) Date of Patent: Sep. 16, 2014

(54) NERVE STIMULATING DEVICE

(71) Applicant: Olympus Corporation, Tokyo (JP)

(72) Inventor: Moe Goto, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/868,219

(22) Filed: Apr. 23, 2013

(65) Prior Publication Data

US 2013/0238057 A1 Sep. 12, 2013

Related U.S. Application Data

(63) Continuation of application No. PCT/JP2011/074678, filed on Oct. 26, 2011.

(30) Foreign Application Priority Data

Oct. 28, 2010 (JP) ................................. 2010-242607

(51) Int. Cl.
*A61N 1/36* (2006.01)

(52) U.S. Cl.
CPC ................................. *A61N 1/36114* (2013.01)
USPC ....................................... 607/62; 607/2; 607/9

(58) Field of Classification Search
CPC ................................................ A61N 1/36114
See application file for complete search history.

(56) References Cited

U.S. PATENT DOCUMENTS 7,869,881 B2 * 1/2011 Libbus et al. .................. 607/44
8,175,705 B2 * 5/2012 Libbus ............................ 607/14

FOREIGN PATENT DOCUMENTS

| JP | 2003-511163 A | 3/2003 |
| JP | 2004-290536 A | 10/2004 |
| JP | 2005-013504 A | 1/2005 |
| JP | 2006-280588 A | 10/2006 |
| JP | 2008-296014 A | 12/2008 |
| JP | 2009-521260 A | 6/2009 |
| JP | 2009-233024 A | 10/2009 |
| WO | 01/26729 A1 | 4/2001 |
| WO | 2007/073455 A1 | 6/2007 |

OTHER PUBLICATIONS

International Search Report dated Jan. 31, 2012 issued in PCT/JP2011/074678, together with an English language translation.

* cited by examiner

*Primary Examiner* — Michael Kahelin
(74) *Attorney, Agent, or Firm* — Scully, Scott, Murphy & Presser, P.C.

(57) ABSTRACT

A vagus nerve is efficiently stimulated while preventing wasteful energy consumption. Provided is a nerve stimulating device (1) including a stimulation-signal outputting portion (3) that outputs a stimulation signal to a vagus nerve (B); a heart-event detecting portion (2) that detects a heart event; and a control portion (4) that makes a judgment regarding the responsiveness of a heart (A) based on the heart event detected by the heart-event detecting portion (2) in response to the stimulation signal output from the stimulation-signal outputting portion (3), and that controls the stimulation-signal outputting portion (3) so that an intensity of the stimulation signal is decreased when the responsiveness of the heart (A) is decreased.

8 Claims, 8 Drawing Sheets

NERVE STIMULATING DEVICE

CROSS-REFERENCE TO RELATED APPLICATIONS

This is a continuation of International Application PCT/JP2011/074678, with an international filing date of Oct. 26, 2011, which is hereby incorporated by reference herein in its entirety. This application claims the benefit of Japanese Patent Application No. 2010-242607, the contents of which are incorporated herein by reference.

TECHNICAL FIELD

The present invention relates to a nerve stimulating device.

BACKGROUND ART

In the related art, there is a known heart treatment device that performs vagus-nerve stimulation by increasing an amplitude or a pulse width of stimulation pulses used for stimulating the vagus nerve when an effect of the vagus-nerve stimulation is judged to be small based on electrocardiographic signals after performing the vagus-nerve stimulation (for example, see Patent Literature 1).

CITATION LIST

Patent Literature

{PTL 1} Japanese Unexamined Patent Application, Publication No. 2006-280588

SUMMARY OF INVENTION

Technical Problem

With the heart treatment device disclosed in Patent Literature 1, because the stimulation pulse energy for the vagus-nerve stimulation is increased when the effect of the vagus-nerve stimulation is judged to be small, stimulation pulses having large energy continue to be applied even when the vagus-nerve stimulation has no effect, and thus, the energy is wasted. In particular, in the case of a battery-driven unit, such as a heart treatment device implanted in the body, the battery is quickly exhausted.

The present invention is to provide a nerve stimulating device that is capable of efficiently stimulating the vagus nerve while preventing wasteful energy consumption.

Solution to Problem

A first aspect of the present invention provides a nerve stimulating device including a stimulation-signal outputting portion that outputs a stimulation signal to a vagus nerve; a heart-event detecting portion that detects a heart event; and a control portion that makes a judgment regarding the responsiveness of a heart based on the heart event detected by the heart-event detecting portion in response to the stimulation signal output from the stimulation-signal outputting portion, and that controls the stimulation-signal outputting portion so that the intensity of the stimulation signal is decreased when the responsiveness of the heart is decreased (First Aspect).

When the stimulation-signal outputting portion is activated and the stimulation signal is output to the vagus nerve, the occurrence of the heart event detected by the heart-event detecting portion becomes less frequent; however, the responsiveness of the heart sometimes is decreased when the stimulation signal is output continuously. In such a case, the occurrence of the heart event becomes more frequent regardless of the output of the stimulation signal.

In the first aspect of the present invention, the control portion may judge whether or not the responsiveness of the heart has recovered after decreasing the intensity of the stimulation signal, and may control the stimulation-signal outputting portion so that the intensity of the stimulation signal is increased when the responsiveness is judged to have recovered. (Second Aspect).

In a second aspect of the present invention, the control portion may make a judgment regarding the recovery of the responsiveness of the heart based on an elapsed time from a time at which the intensity of the stimulation signal is decreased (Third Aspect).

In addition, in the second aspect of the present invention, the heart-event detecting portion may detect heartbeats; and the control portion may calculate a heart rate by using the heartbeats detected by the heart-event detecting portion, and also may make a judgment regarding the recovery of the responsiveness of the heart based on a ratio of the heart rate to a heart rate at a time at which the intensity of the stimulation signal is decreased (Fourth Aspect).

Because the heart rate increases regardless of the stimulation signal when the responsiveness of the heart is decreased, the heart rate starts to increase from the time at which the signal intensity is decreased when the signal intensity is decreased.

In addition, in the second aspect of the present invention, the heart-event detecting portion may detect heartbeats; and the control portion may calculate a heart rate by using the heartbeats detected by the heart-event detecting portion, and also may make a judgment regarding the recovery of the responsiveness of the heart based on the calculated heart rate (Fifth Aspect).

Because the heart rate increases regardless of the stimulation signal when the responsiveness of the heart is decreased, the heart rate starts to increase from the time at which the signal intensity is decreased when the signal intensity is decreased.

In addition, in a third aspect of the present invention, when the recovery of the responsiveness of the heart is judged to be insufficient based on the heart event detected by the heart-event detecting portion after the intensity of the stimulation signal is increased, the control portion may increase the elapsed time to be used for making the judgment regarding the recovery of the responsiveness (Sixth Aspect).

In addition, in a fourth aspect of the present invention, when the recovery of the responsiveness of the heart is judged to be insufficient based on the heart event detected by the heart-event detecting portion after the intensity of the stimulation signal is increased, the control portion may increase the ratio to be used for making the judgment regarding the recovery of the responsiveness (Seventh Aspect).

In addition, in a fifth aspect of the present invention, when the recovery of the responsiveness of the heart is judged to be insufficient based on the heart event detected by the heart-event detecting portion after the intensity of the stimulation signal is increased, the control portion may increase the heart rate to be used for making the judgment regarding the recovery of the responsiveness (Eighth Aspect).

DESCRIPTION OF EMBODIMENT

A nerve stimulating device 1 according to an embodiment of the present invention will be described below with reference to the drawings.

Figure 1:
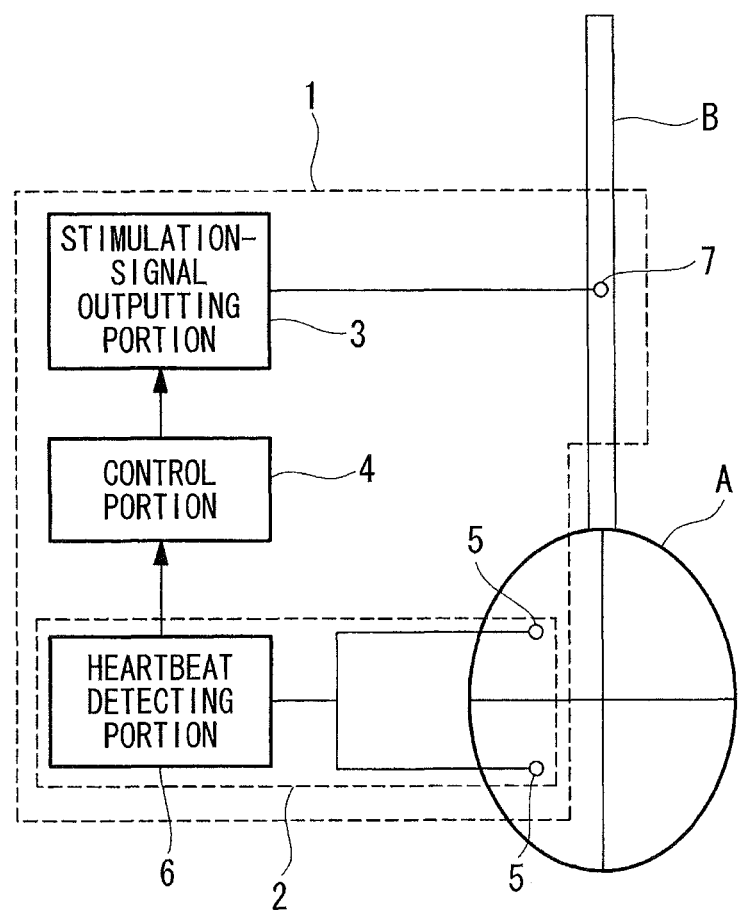
FIG. 1 is an overall configuration diagram schematically showing a nerve stimulating device according to an embodiment of the present invention.

As shown in FIG. 1, the nerve stimulating device 1 according to this embodiment is provided with a heart-event detecting portion 2 that detects a heart event, that is, an event that occurs in a heart A, for example, a heartbeat; a stimulation-signal outputting portion 3 that outputs stimulation signals to a vagus nerve B; and a control portion 4 that controls the stimulation-signal outputting portion 3 in accordance with the heart event detected by the heart-event detecting portion 2.

The heart-event detecting portion 2 is provided with lead electrodes 5 that are placed on the heart A and a heartbeat detecting portion 6 that detects heart events in the form of heartbeats based on electrocardiographic signals, that is, electric potentials at the lead electrodes 5. The heartbeat detecting portion 6 detects heartbeats assuming that depolarization occurs in the heart when the magnitude of the electric potentials at the lead electrodes 5 or the rate of change thereof exceeds a predetermined threshold.

Figure 2A:
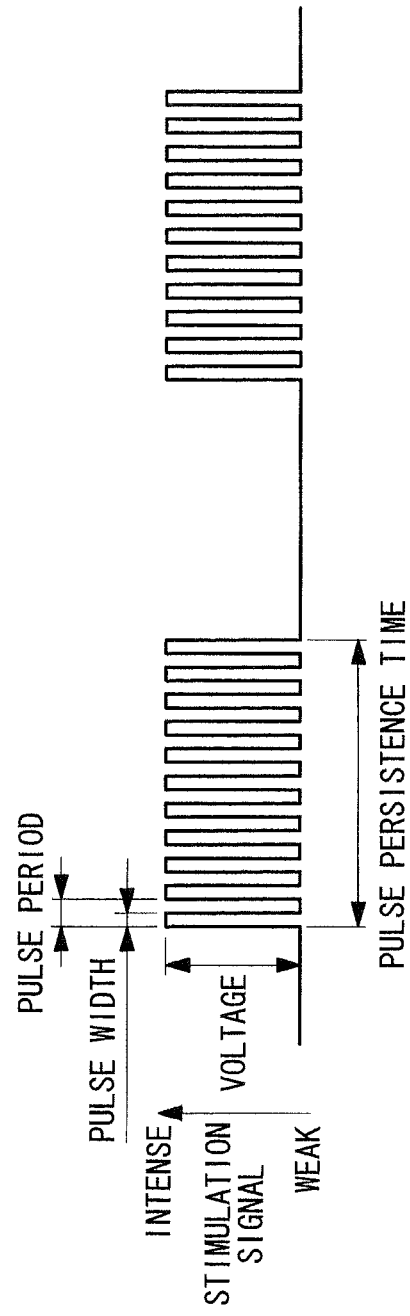
FIG. 2A is a diagram showing an example pulse train of stimulation signals output from the nerve stimulating device in FIG. 1.

The stimulation-signal outputting portion 3 is connected to a nerve stimulating lead 7 attached to the vagus nerve B, generates a stimulation-pulse train for electrically stimulating the vagus nerve B, and supplies it to the vagus nerve B via the nerve stimulating lead 7. As shown in FIG. 2A, parameters of the stimulation-pulse train include voltage, pulse width, pulse period, and pulse persistence time, and the intensity of the stimulation signals can be adjusted by changing them.

Figure 2B:
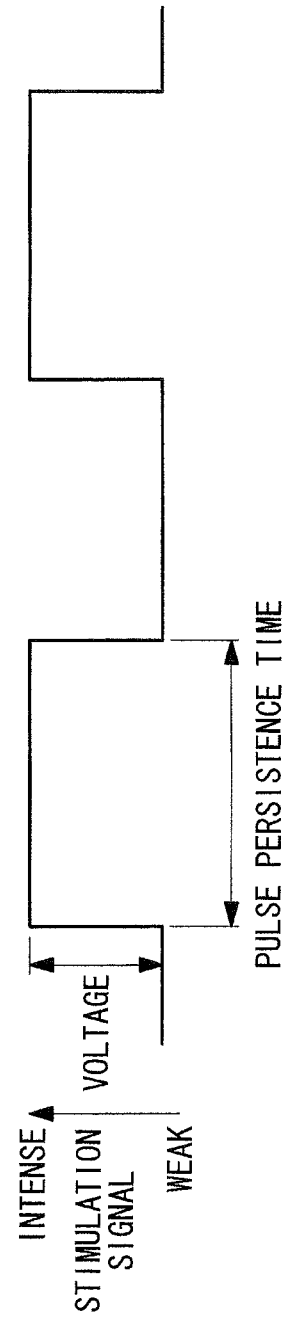
FIG. 2B is a diagram showing a simplified display of FIG. 2A.

In the following descriptions, in order to make the drawings clearer, a pulse train in which numerous pulses are output, as in FIG. 2A, is simplified so that the plurality of continuous pulses are consolidated and displayed as a single rectangular wave, as shown in FIG. 2B.

The control portion 4 calculates a heart rate from the timing of the heartbeats detected by the heart-event detecting portion 2, and makes a judgment regarding the need for stimulating the vagus nerve based on the heart rate. For examples, when the heart rate is equal to or greater than a predetermined threshold, the control portion 4 commands the stimulation-signal outputting portion 3 to output the stimulation signals, and the stimulation-signal outputting portion 3 outputs the stimulation signals having preset parameters based on the command.

Then, with the nerve stimulating device 1 according to this embodiment, the control portion 4 monitors the heart rate during a set stimulation-persistence time, and makes a judgment regarding the responsiveness of the heart A. That is, the control portion 4 makes a judgment that the responsiveness of the heart A is high with respect to the stimulation of the vagus nerve B if the heart rate is equal to or lower than a predetermined threshold P1 during the stimulation-persistence time, during which the stimulation signals are continuously output, and makes a judgment that the responsiveness of the heart A has been decreased if the heart rate increases beyond the predetermined threshold P1.

Regardless of the output of the stimulation signals, when the responsiveness of the heart A is judged to have been decreased, the control portion 4 instructs the stimulation-signal outputting portion 3 to stop the output of the stimulation-signals. Furthermore, when a predetermined amount of time T1 has passed after the output of the stimulation signals is stopped, the control portion 4 makes a judgment that the responsiveness of the heart A has recovered, and instructs the stimulation-signal outputting portion 3 to resume the output of the stimulation signals. The predetermined amount of time T1 should be measured in advance when the nerve stimulating lead 7 of the nerve stimulating device 1 is implanted, at the time of examination, or the like, and it should be set in the control portion 4.

The operation of the thus-configured nerve stimulating device 1 according to this embodiment will be described below.

To stimulate the vagus nerve B by using the nerve stimulating device 1 according to this embodiment, the lead electrodes 5 are disposed on the heart A and the nerve stimulating lead 7 is disposed on the vagus nerve B.

Figure 3:
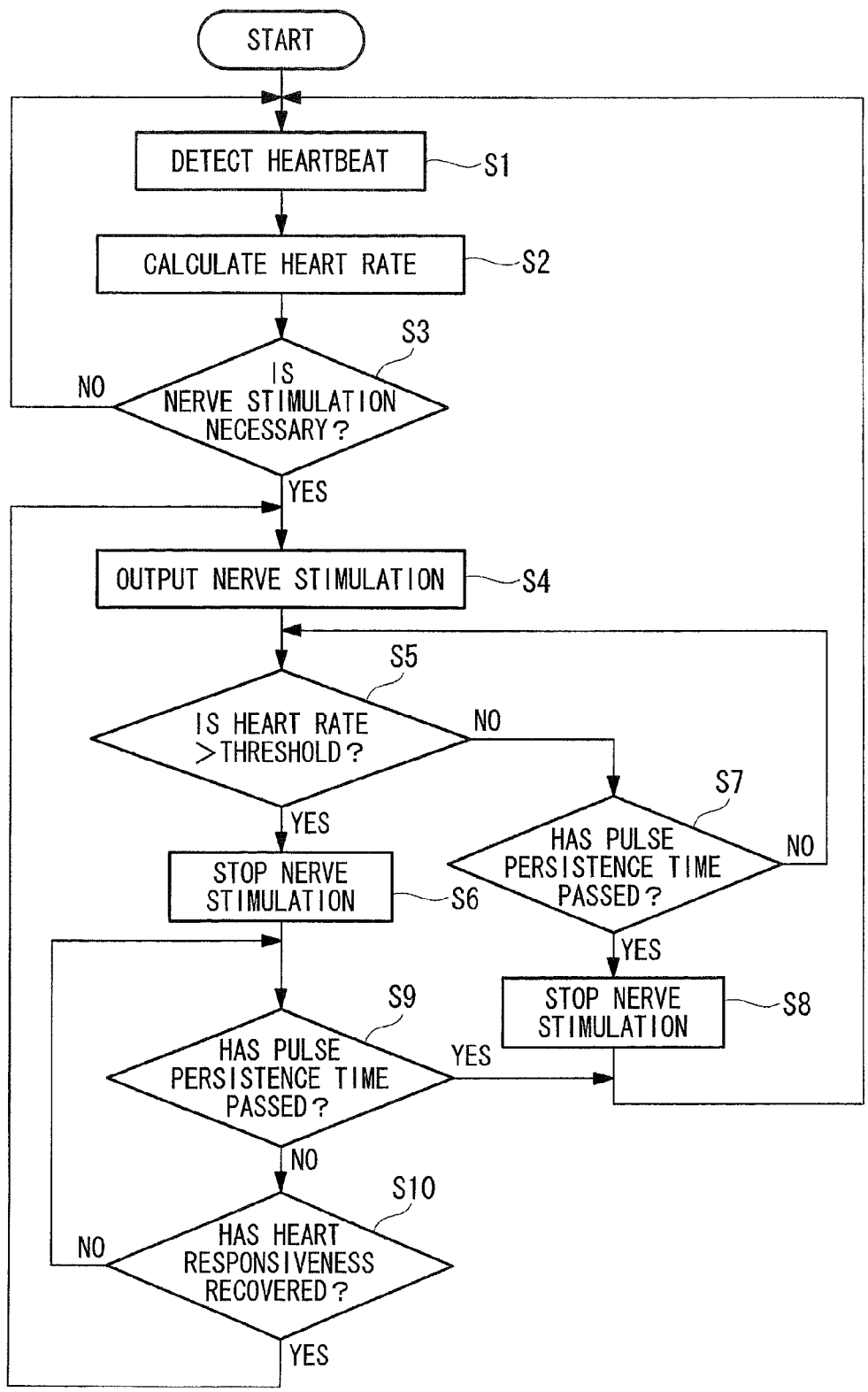
FIG. 3 is a flowchart for explaining the procedure of nerve stimulation performed by the nerve stimulating device in FIG. 1.

Then, as shown in FIG. 3, the heart-event detecting portion 2 detects the electric potentials at the lead electrodes 5, and the heartbeat detecting portion 6 detects heartbeats (Step S1). The detected heartbeats are transmitted to the control portion 4, and the control portion 4 calculates the heart rate from the timing of the heartbeats (Step S2).

The control portion 4 constantly monitors the heart rate; the nerve stimulation is judged to be necessary when the heart rate exceeds the predetermined threshold; and the nerve stimulation is judged to be unnecessary when the heart rate is equal to or lower than the predetermined threshold (Step S3).

Then, when the nerve stimulation is judged to be necessary, a command is given to the stimulation-signal outputting portion 3 so that stimulation signals formed of stimulation-pulse trains in accordance with the preset parameters are output to the vagus nerve B via the nerve stimulating lead 7 (Step S4).

Once the stimulation signals are supplied to the vagus nerve B, the heart A lowers the heart rate in response thereto. Accordingly, it is possible to achieve a stimulating effect on the vagus nerve B, which inhibits tachycardia.

In this case, depending on the state of the heart A of a patient, the heart-rate reduction effect sometimes diminishes, that is, the responsiveness of the heart A is decreased, even though the stimulation signals continue to be supplied.

The control portion 4 judges whether or not the heart rate is above the predetermined threshold P1 (Step S5), and, if the threshold is exceeded, a command is given to the stimulation-signal outputting portion 3 so as to stop the output of the stimulation signals (Step S6).

When the heart rate is equal to or lower than the predetermined threshold P1, the control portion 4 judges whether or not the pulse persistence time has passed (Step S7), and, if the pulse persistence time has not passed, the monitoring of the heart rate (Step S5) is repeated. On the other hand, if the pulse persistence time has passed, a command is given to the stimulation-signal outputting portion 3 so as to stop the output of the stimulation signals (Step S8), and the steps from Step S1 are repeated.

In addition, when the output of the stimulation signals is stopped because the heart rate exceeds the predetermined threshold P1, it is judged whether or not the pulse persistence time has passed (Step S9), and, if it has not passed, it is judged whether or not the responsiveness of the heart A has recovered (Step S10). The responsiveness of the heart A is judged to have recovered if the predetermined amount of time T1 has passed after the output of the stimulation signals is stopped, and the steps from Step S4 are repeated.

On the other hand, when the responsiveness of the heart A has not recovered, the steps from Step S9 are repeated. When the pulse persistence time has passed without the responsiveness of the heart A having recovered, the steps from Step S1 are repeated.

In this way, with the nerve stimulating device 1 according to this embodiment, because the output of the stimulation signals is stopped, instead of outputting even more intense stimulation signals, when the stimulating effect on the vagus nerve B diminishes while the stimulation signals are output continuously, it is possible to prevent wasteful power consumption in a situation in which no effect is expected.

Figure 4:
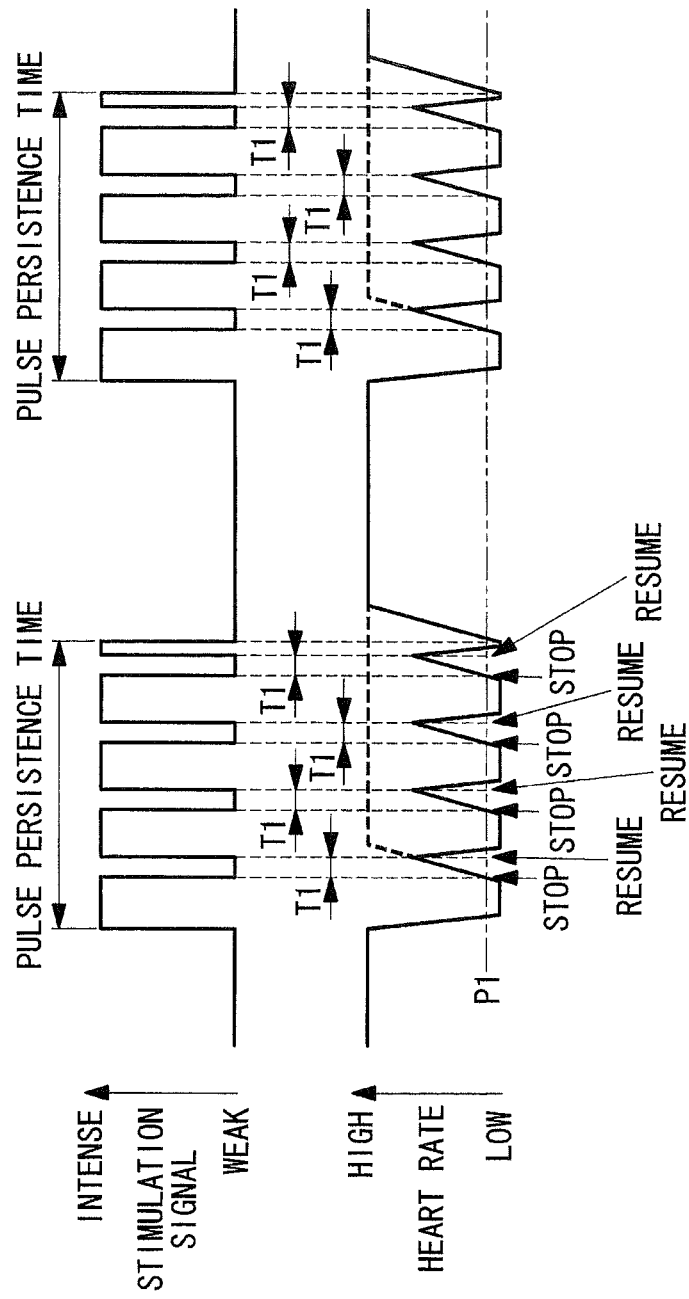
FIG. 4 is a diagram showing changes in the stimulation signals and heart rate caused by the nerve stimulating device in FIG. 1.

In addition, with the nerve stimulating device 1 according to this embodiment, because the output of the stimulation signals is resumed after waiting for the responsiveness of the heart A to recover in the state in which the output of the stimulation signals is stopped, there is an advantage in that an effective stimulating effect on the vagus nerve B can be achieved, as indicated by the solid line in FIG. 4. That is, even when the heart A is in a state in which the responsiveness of the heart A is decreased even though the stimulation signals are being output, it is possible to obtain a maximum stimulating effect on the vagus nerve B while preventing wasteful power consumption. In FIG. 4, the broken line shows the heart rate when the nerve stimulation continues to be stopped without resuming it.

In this case, because the recovery of the responsiveness of the heart A is judged based on the elapsed time T1 from the time at which the output of the stimulation signals is stopped, the judgment can be made in a simple manner irrespective of the heart rate.

Figure 5:
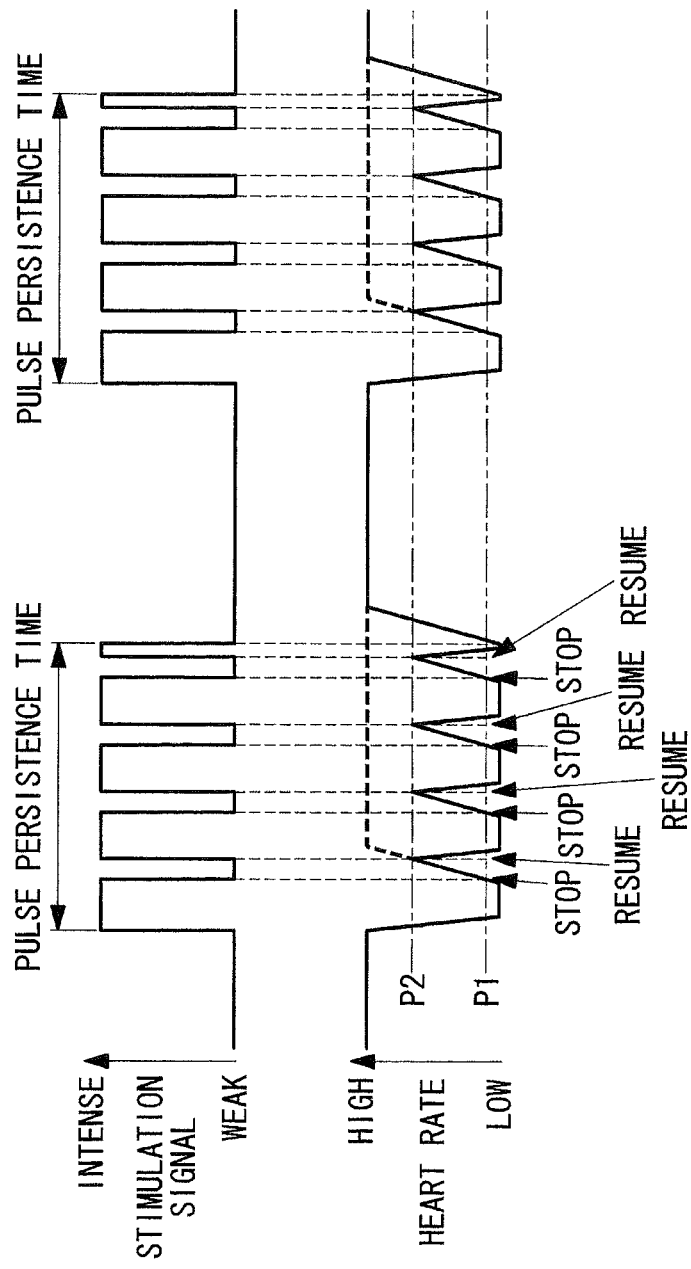
FIG. 5 is a diagram showing changes in the stimulation signals and heart rate caused by a first modification of the nerve stimulating device in FIG. 1.

In this embodiment, instead of making a judgment regarding the recovery of the responsiveness of the heart A based on the elapsed time T1 from the time at which the output of the stimulation signals is stopped, the judgment may be made based on an absolute value P2 of the heart rate or a ratio (P2/P1) thereof with respect to a heart rate P1 at the time at which the output of the stimulation signals is stopped, as shown in FIG. 5. By doing so, as with the elapsed time T1, the recovery of the responsiveness of the heart A can be judged in a simple manner based on the heartbeats that are detected continuously. By doing so, the responsiveness of the heart can be judged to have recovered in a simple manner at a time when the ratio (P2/P1) of the heart rate has increased to a predetermined value, and the vagus nerve B can be effectively stimulated in a state in which the responsiveness of the heart A has recovered. Because the heart rate at the time when the intensity of the stimulation signal is decreased is used as a reference, the recovery of the responsiveness of the heart A can be judged even when the heart rate is unstable, and when it is high or low overall.

In addition, with the nerve stimulating device 1 according to this embodiment, the control portion 4 may make a judgment regarding the recovery of the responsiveness of the heart based on the calculated heart rate.

Because the heart rate increases regardless of the stimulation signal when the responsiveness of the heart A is decreased, the heart rate starts to increase from the time at which the signal intensity is decreased when the signal intensity is decreased. Therefore, by doing so, the responsiveness of the heart A can be judged to have recovered in a simple manner at a time when the heart rate has increased to a predetermined value, and the vagus nerve can be effectively stimulated in a state in which the responsiveness of the heart has recovered.

Figure 6:
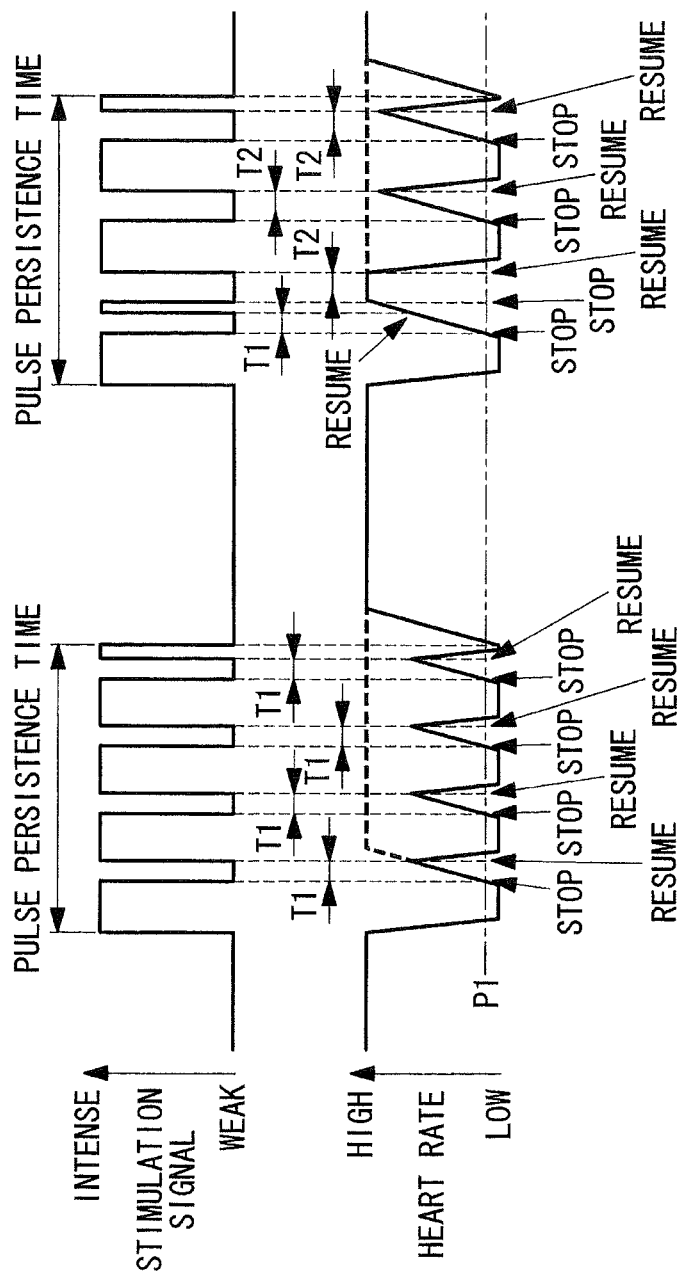
FIG. 6 is a diagram showing changes in the stimulation signals and heart rate caused by a second modification of the nerve stimulating device in FIG. 1.

In addition, when the recovery of the responsiveness of the heart A is judged based on the elapsed time T1, the responsiveness of the heart A sometimes has not actually recovered, and thus, the heart rate is not decreased even after resuming the stimulation of the vagus nerve B. In such a case, as shown in FIG. 6, the output of the stimulation signals may be stopped immediately, and the elapsed time for making the judgment regarding the recovery of the responsiveness of the heart A may be extended from the time T1 to a time T2.

By doing so, there is an advantage in that it is possible to wait sufficiently long for the responsiveness of the heart A to recover in the state in which the stimulation signals are stopped, and thus, it is possible to achieve a stimulating effect on the vagus nerve B more reliably.

Figure 7:
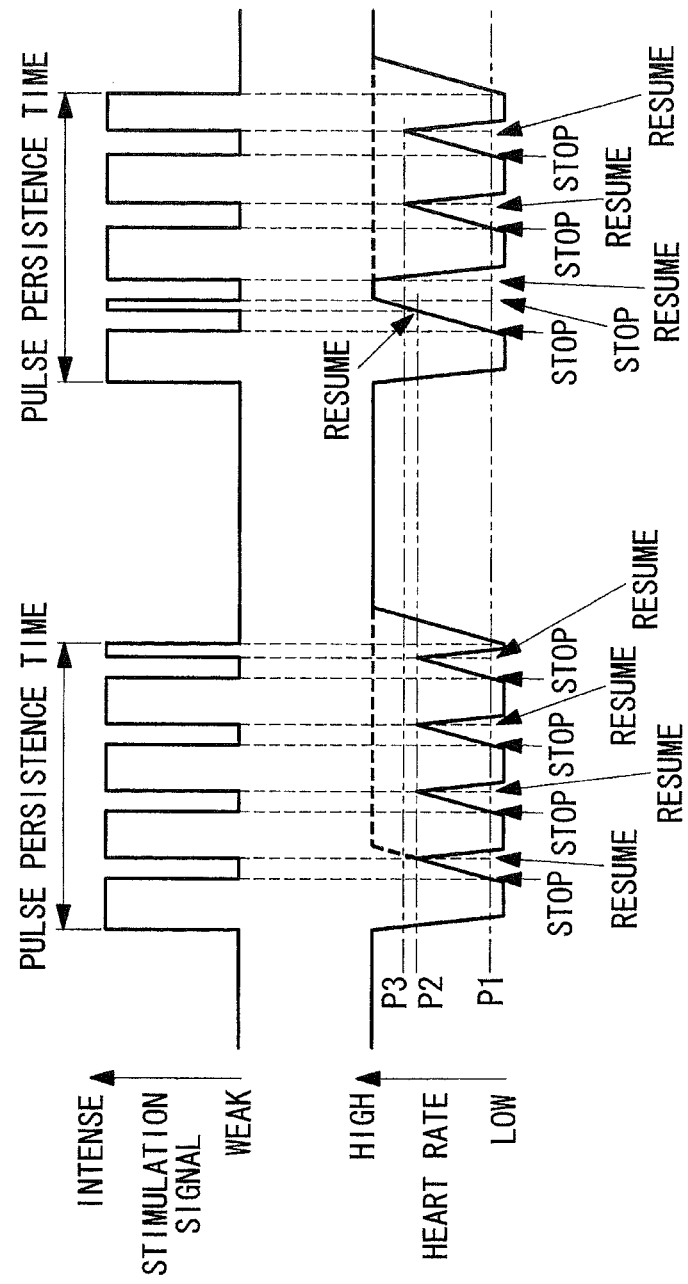
FIG. 7 is a diagram showing changes in the stimulation signals and heart rate caused by a third modification of the nerve stimulating device in FIG. 1.

In addition, also when judging the recovery of the responsiveness of the heart A based on the absolute value P2 of the heart rate or the ratio (P2/P1) thereof with respect to the heart rate P1 at the time at which the output of the stimulation signals is stopped, if the responsiveness of the heart A has not recovered even after resuming the output of the stimulation signals, as with the case of the elapsed time, the heart rate used for making the judgment regarding the recovery of the responsiveness of the heart A may be increased from the heart rate P2 to a heart rate P3, as shown in FIG. 7. By doing so, there is an advantage in that, as with the extension of the elapsed time, it is possible to wait sufficiently long for the responsiveness of the heart A to recover, and thus, it is possible to achieve a stimulating effect on the vagus nerve B more reliably.

In addition, in this embodiment, although the output of the stimulation signals to the vagus nerve B is stopped when the responsiveness of the heart A is judged to have been decreased, alternatively, the intensity (voltage) of the stimulation signals may be decreased. It is possible to alleviate the impact on the vagus nerve B as compared with abruptly stopping the output of the stimulation signals.

According to this embodiment, it is possible to efficiently stimulate the vagus nerve while preventing wasteful energy consumption.

REFERENCE SIGNS LIST

A heart
B vagus nerve
P1, P2, P3 heart rate
T1, T2 time (elapsed time)
1 nerve stimulating device
2 heart-event detecting portion
3 stimulation-signal outputting portion
4 control portion

The invention claimed is:
1. A nerve stimulating device comprising:
a stimulation-signal outputting portion that outputs a stimulation signal to a vagus nerve;

a heart-event detecting portion that detects a heart event; and a control portion that makes a judgment regarding the responsiveness of a heart based on the heart event detected by the heart-event detecting portion in response to the stimulation signal output from the stimulation-signal outputting portion, and that controls the stimulation-signal outputting portion so that an intensity of the stimulation signal is decreased when the responsiveness of the heart is decreased.

2. The nerve stimulating device according to claim 1, wherein the control portion judges whether or not the responsiveness of the heart has recovered after decreasing the intensity of the stimulation signal, and controls the stimulation-signal outputting portion so that the intensity of the stimulation signal is increased when the responsiveness is judged to have recovered.

3. The nerve stimulating device according to claim 2, wherein the control portion makes a judgment regarding the recovery of the responsiveness of the heart based on an elapsed time from a time at which the intensity of the stimulation signal is decreased.

4. The nerve stimulating device according to claim 2, wherein the heart-event detecting portion detects heartbeats; and wherein the control portion calculates a heart rate by using the heartbeats detected by the heart-event detecting portion, and also makes a judgment regarding the recovery of the responsiveness of the heart based on a ratio of the heart rate to a heart rate at a time at which the intensity of the stimulation signal is decreased.

5. The nerve stimulating device according to claim 2, wherein the heart-event detecting portion detects heartbeats; and wherein the control portion calculates a heart rate by using the heartbeats detected by the heart-event detecting portion, and also makes a judgment regarding the recovery of the responsiveness of the heart based on the calculated heart rate.

6. The nerve stimulating device according to claim 3, wherein, when the recovery of the responsiveness of the heart is judged to be insufficient based on the heart event detected by the heart-event detecting portion after the intensity of the stimulation signal is increased, the control portion increases the elapsed time to be used for making the judgment regarding the recovery of the responsiveness.

7. The nerve stimulating device according to claim 4, wherein, when the recovery of the responsiveness of the heart is judged to be insufficient based on the heart event detected by the heart-event detecting portion after the intensity of the stimulation signal is increased, the control portion increases the ratio to be used for making the judgment regarding the recovery of the responsiveness.

8. The nerve stimulating device according to claim 5, wherein, when the recovery of the responsiveness of the heart is judged to be insufficient based on the heart event detected by the heart-event detecting portion after the intensity of the stimulation signal is increased, the control portion increases the heart rate to be used for making the judgment regarding the recovery of the responsiveness.

\* \* \* \* \*